United States Patent [19]

Powers Jr.

[11] Patent Number: 5,464,397
[45] Date of Patent: Nov. 7, 1995

[54] BACTERIA VALVE

[76] Inventor: Carleton A. Powers Jr., 2268 68th St. SE., Caledonia, Mich. 49316

[21] Appl. No.: 180,046

[22] Filed: Jan. 11, 1994

[51] Int. Cl.⁶ ........................................ A61M 5/00
[52] U.S. Cl. ..................... 604/246; 604/280; 604/283; 433/95
[58] Field of Search .................. 604/30, 246, 264, 604/265, 268, 313, 322, 323, 335, 350, 905, 283; 433/91, 95, 96; 137/140, 142

[56] References Cited

U.S. PATENT DOCUMENTS

| | | |
|---|---|---|
| 2,274,893 | 3/1942 | Freedman . |
| 3,332,422 | 7/1967 | Jinkens et al. ........................ 128/275 |
| 3,476,144 | 11/1969 | Krantz . |
| 3,482,313 | 12/1969 | Stram . |
| 3,863,635 | 2/1975 | Swatman . |
| 3,906,935 | 9/1975 | Raia et al. ............................. 128/2 F |
| 4,022,228 | 5/1977 | Riddick . |
| 4,083,115 | 4/1978 | McKelvey . |
| 4,083,706 | 4/1978 | Wiley ....................................... 55/385 R |
| 4,232,677 | 11/1980 | Leibinsohn ........................ 128/350 R |
| 4,586,900 | 5/1986 | Hymanson et al. ................... 433/96 |
| 4,589,869 | 5/1986 | Wernborg . |
| 4,865,545 | 9/1989 | LaRocca . |
| 4,886,492 | 12/1989 | Brooke . |
| 5,078,603 | 1/1992 | Cohen . |
| 5,269,769 | 12/1993 | Dhara et al. ............................ 604/264 |

FOREIGN PATENT DOCUMENTS 445091  4/1991  England .
394252  6/1933  United Kingdom .

OTHER PUBLICATIONS

Exhibit A is literature published by SurgiMark Inc. of Yakima, Washington regarding medical yankauer tips.

Primary Examiner—Corrine M. Maglione
Assistant Examiner—Bryan L. Tsosie
Attorney, Agent, or Firm—Price, Heneveld, Cooper, Dewitt & Litton

[57] ABSTRACT

A valve is provided for preventing backflow of bacteria and other unhealthy substances in a medical suctioning apparatus. The valve includes a chamber and a tubular member positionable in the chamber having one or more reversely lipped fins. The chamber and tubular member provide a tortuous path that effectively limits backflow of bacteria and other unhealthy substances. Various modifications of the valve are disclosed including two, three and four piece valves. The valves are configured to be positioned between a medical suctioning unit and a patient-contacting part such as ejectors, evacuators, and medical yankauers. The valve shapes facilitate manufacture, and can be made of disposable or autoclavable materials.

30 Claims, 4 Drawing Sheets

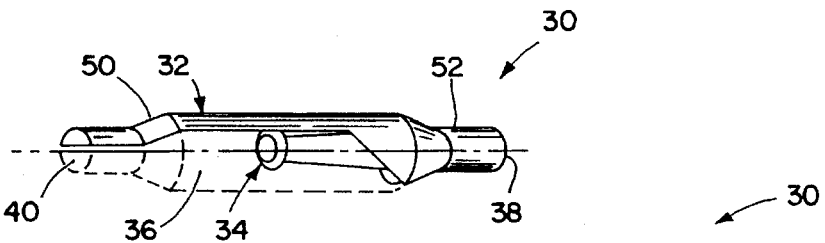
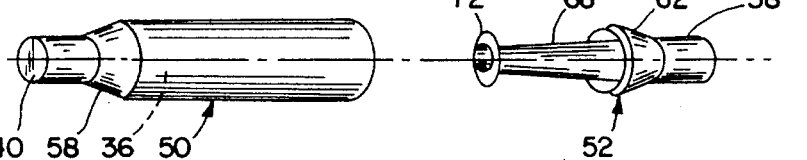
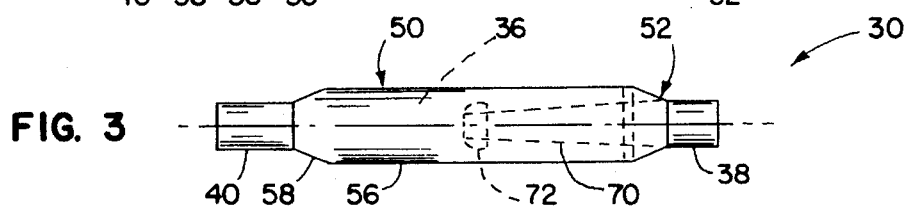
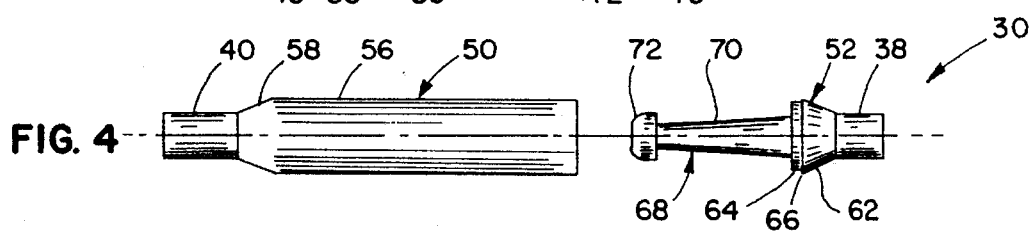
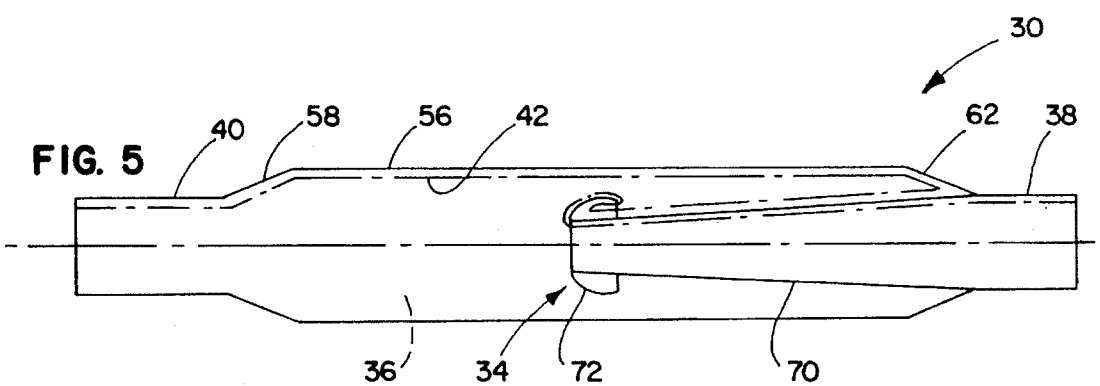
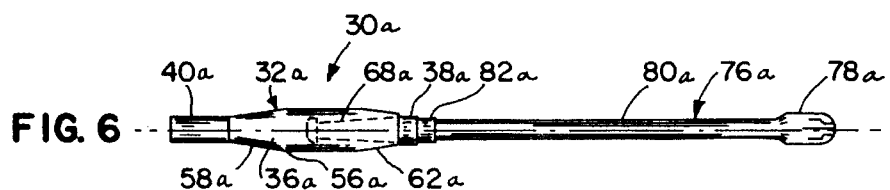

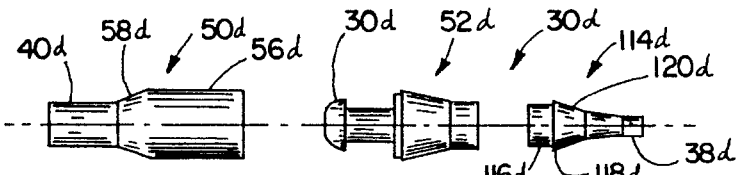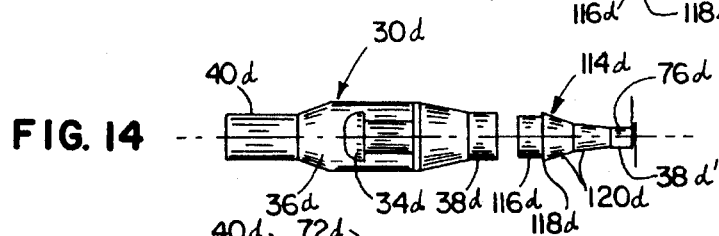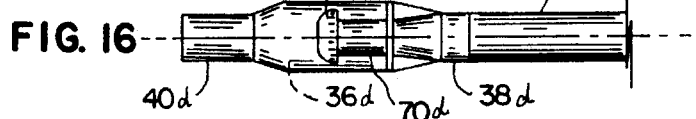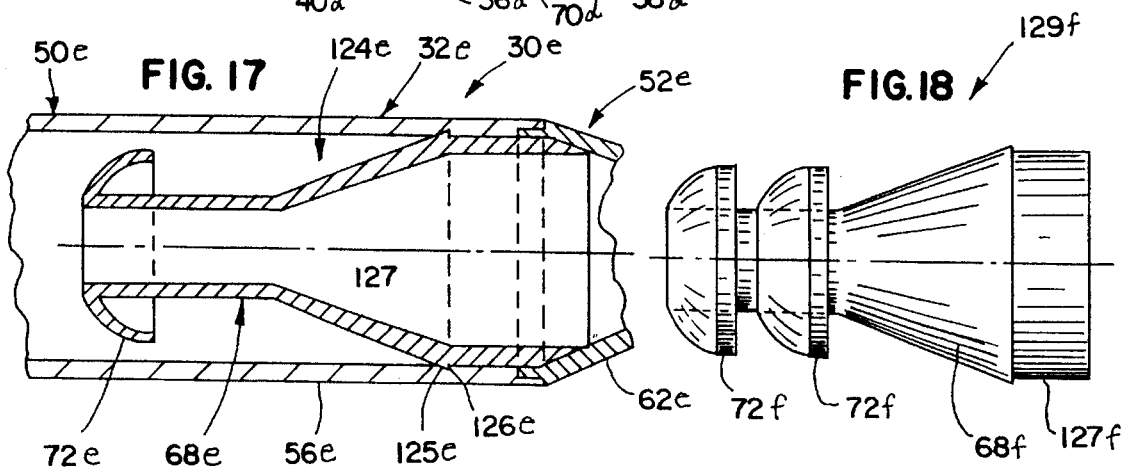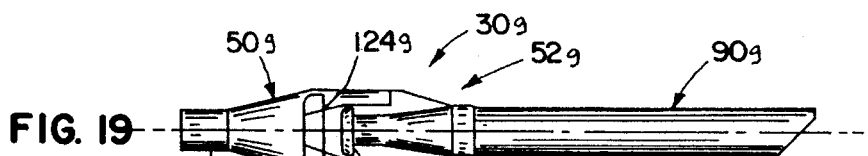

5,464,397

BACTERIA VALVE

BACKGROUND OF THE INVENTION

The present invention concerns a valve for medical suctioning apparatus, and more particularly concerns a valve configured to effectively prevent backflow of body fluid and undesired movement of bacteria and other unhealthy substances in the medical suctioning apparatus.

Medical centers, hospitals, dental practices and other medical operations commonly use suction apparatus to remove body fluids such as saliva or blood during medical procedures. These body fluids can carry or become contaminated with bacteria and other unhealthy substances, such that it is very important to prevent the body fluids, bacteria and other unhealthy substances from backflowing or moving in a reverse direction into any patient. This can be problematic since substances such as bacteria will travel along surfaces without the assistance of a fluid carrier. For example, even if the part of the medical suctioning apparatus that contacts a patient is replaced with each new patient, bacteria can travel in a reverse direction through the new part and thus still cause a problem. Therefore, particularly in view of modern public concern over communicable diseases and diseases that can be transmitted by body fluids, it is important that maximum protection against undesired backflow and/or movement of bacteria be provided.

In U.S. Pat. No. 4,083,706 to Wiley in FIG. 1 there is disclosed a sterile trap accessory that can be inserted between a suctioning conduit and an aspirator. The trap accessory includes a filter for catching debris, and a tubular section that protrudes into the trap toward the filter. The filter effectively captures debris for later viewing by a medical worker or doctor, however in doing so large amounts of debris are held in the trap accessory thus potentially increasing the risk of bacteria movement in a reverse direction. Further, the surfaces between the filter and the inlet to the trap accessory do not provide as arduous of a path for preventing backflow of bacteria as desired.

Thus, a valve for preventing backflow of bacteria and other undesirable substances is desired.

SUMMARY OF THE INVENTION

The present invention includes an antibacteria valve for preventing undesired movement and backflow of bacteria and other unhealthy substances. The valve includes an elongated casing defining a longitudinal direction and a chamber, the casing including an inlet and an outlet to the chamber. A tubular member projects into the chamber from one of the inlet and the outlet. The elongated casing and the tubular insert define an unobstructed path for body fluids to flow from the inlet to the outlet, but include surfaces defining an arduous path for bacteria moving from the outlet to the inlet. Thus, body fluids can be readily suctioned through the valve from the inlet to the outlet, but bacteria cannot readily backflow through the valve due to the tortuous path defined by the casing and the tubular member. In a preferred form, the valve includes an end section having a ring-shaped fin extending radially in the casing, the chamber and the ring-shaped fin combining to define the tortuous path for backflowing bacteria.

These and other features and advantages of the present invention will be further understood by a person of ordinary skill in the art by reference to the following, specification, claims and appended drawings.

BRIEF DESCRIPTION OF THE DRAWINGS

FIG. 1 is a partially broken-away perspective view of an antibacteria valve embodying the present invention;

FIG. 2 is an exploded perspective view of the valve in FIG. 1;

FIG. 3 is a side view of the valve shown in FIG. 1;

FIG. 4 is an exploded side view of the valve shown in FIG. 3;

FIG. 5 is an enlarged cross-sectional view of the valve shown in FIG. 1 showing the tortuous path defined by the valve inner surfaces which prevents backflow of bacteria through the valve;

FIG. 6 is a side view of a second assembly embodying the present invention including a modified second valve releasably connected to a flexible deformable saliva ejector;

FIG. 13 is an exploded view of a modified fifth valve embodying the present invention, the valve being three pieces and including an adaptor for converting the valve for use with either an ejector or an evacuator;

FIG. 14 is a partially exploded view of the valve shown in FIG. 13, the adapter tip being shown as exploded away but as being ready for attachment to the valve;

FIG. 15 is a side view of the assembly shown in FIG. 13;

FIG. 16 is a side view of the assembly shown in FIG. 13 assembled to an evacuator, the adapter tip having been removed;

FIG. 17 is a fragmentary side view of a sixth valve embodying the present invention, the valve including an insert including a ring-shaped fin;

FIG. 18 is a side view of a second insert for a seventh valve, the insert including a pair of ring-shaped fins;

FIG. 19 is a side view of an assembly embodying the present invention including an eighth valve, the valve being a three piece valve including a pair of mateable inserts each including a ring-shaped fin and being connected to a disposable oral evacuator;

FIG. 20 is an exploded view of the assembly shown in FIG. 19;

DETAILED DESCRIPTION OF THE PREFERRED EMBODIMENT

Figure 7:
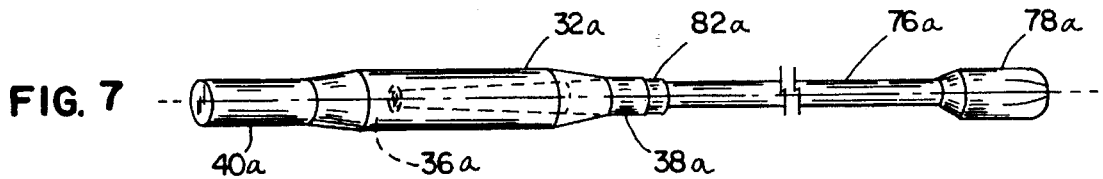
FIG. 7 is a perspective of view of the assembly shown in FIG. 6.

An antibacteria valve 30 (FIGS. 1–4) embodying the present invention includes a casing 32 and a tortuous-path-forming member 34 located in casing 32. Casing 32 includes inner surfaces defining a chamber 36, and an inlet 38 and an outlet 40 located at opposite ends of chamber 36. Valve 30 is particularly constructed to allow flow of body fluids through valve 30 from inlet 38 to outlet 40, but is constructed to provide a tortuous path 42 (FIG. 5) to inhibit undesired movement and/or backflow of bacteria and other unhealthy substances from outlet 40 to inlet 38. Notably, the "tortuous path" method of preventing backflow of bacteria is based on Pasteur's theory of curved paths for protection from germs; however I have been unable to find a commercially available valve utilizing this theory in the manner of the present invention. It is contemplated that these valves can be made from disposable or autoclavable materials such as polymeric materials.

Valve 30 (FIG. 4) is a two piece assembly including a first member 50 and a second member 52 configured to be press fit to first member 50 to frictionally engage and form a leak free joint with first member 50. First member 50 is tubular and includes the outlet 40, a cylindrically-shaped wall 56 of larger diameter than outlet 40, and a frustoconically-shaped section 58 connecting outlet 40 and cylindrically-shaped wall 56. Second member 52 includes the inlet 38, and a frustoconically-shaped section 62 extending from inlet 38. The edge of frustoconically-shaped section 62 is configured to mateably engage the end of cylindrically-shaped wall 56. In particular, the end of frustoconically-shaped section 62 includes a ring 64 configured to press-fittingly engage the inside of the end of cylindrically-shaped wall 56, and further includes an abutting ring 66 configured to engage the end of cylindrically-shaped wall 56 to prevent over-insertion of second member 52 into first member 50. Second member 52 further includes a tubular protruding section 68 that extends from inlet 38 into chamber 36. Tubular protruding section 68 includes an inwardly tapered elongated wall section 70 having a reversely oriented ring-shaped fin 72 on its end that protrudes radially into chamber 36. Ring-shaped fin 72 is preferably oriented at an acute angle to longitudinal centerline 74 and is reversely formed and arcuately shaped so that it extends backwardly toward inlet 38, although it is noted that the angle and shape of ring-shaped fin 72 can be varied for optimal results in specific applications.

When first and second members 50 and 52 are assembled, casing 32 is defined by cylindrically-shaped wall 56, frustoconically-shaped section 58, and frustoconically-shaped section 62. Tortuous path forming member 34 is defined by tubular protruding section 68 including fin 72. As shown in FIG. 5, the inner surfaces of casing 36 and the surfaces of elongated wall section 70 and fin 72 advantageously form tortuous path 42. The tortuous path 42 prevents undesired movement of bacteria in a counterflow direction through valve 30 in large part because bacteria tends to grow or move along surfaces, or tends to otherwise move in linear paths when moving without the assistance of a flowing carrier fluid.

Advantageously, an antibacteria valve such as valve 30 can be used with a variety of different medical suctioning devices. Further, the valve can be formed in different sizes, shapes and configurations to optimize flow-through characteristics and to facilitate assembly of the valve. The following discussion discloses a variety of valve configurations. To reduce repetitive discussion, comparable items and features in the following discussion are labeled with identical numbers used for valve 30, but with the addition of letters "a", "b", "c", and etc.

Figure 8:
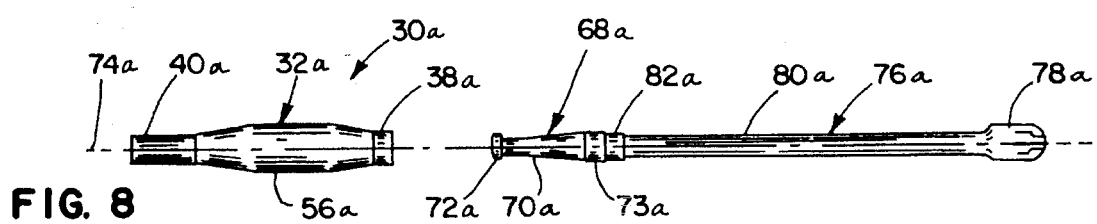
FIG. 8 is an exploded side view of the assembly shown in FIG. 6.

In FIGS. 6 and 7, a valve 30a is shown attached to an ejector 76a such as is commonly used to remove saliva from a patient's mouth. Ejector 76a includes a slotted ejector tip 78a, an elongated deformable tubular straw 80a, and a press fit releasably engageable connector 82a configured to telescopingly frictionally engage inlet 38a on valve 30a. FIG. 8 shows casing 32a exploded away from ejector 76a, but aligned for connection thereto. Valve 30a includes a one-piece casing 32a having an enlarged mid-section 56a, an inlet 38a, and an outlet 40a. Frustoconically-shaped sections 58a and 62a connect inlet 38a and outlet 40a to mid-section 56a, respectively. A tubular second piece or insert 34a is attached to and extends from connector 82a of ejector 76a. Insert 68a includes an elongated wall section 70a including a bulbous section 73a for sealingly engaging the inside of inlet 38a. Bulbous section 73a further has a diameter chosen to sealingly engage the outside of connector 82a. A ring-shaped fin 72a is located on the end of elongated wall section 70a. Ring shaped fin 72a is configured to telescope into chamber 36a through inlet 38a. A tortuous path is thus defined along the inner surfaces of valve 30a, which tortuous path prevents backflow of bacteria. It is noted that casing 32a is a one-piece molding made, for example, by blow molding or roto-molding. However, casing 32a could also be constructed from a pair of injection molded opposing halves (not specifically shown) which mate along a plane that extends parallel and through center line 74a of chamber 36a.

Figure 9:
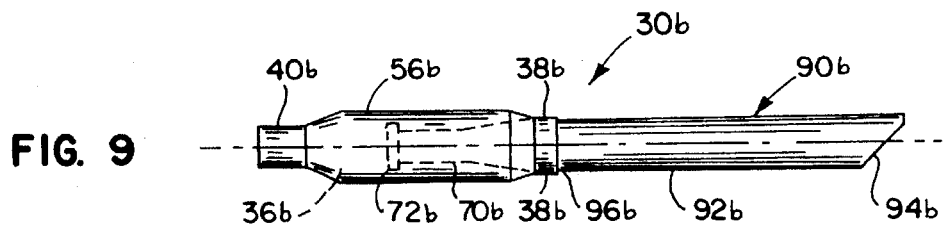
FIG. 9 is a side view of another assembly embodying the present invention including a modified third valve releasably connected to a disposable oral evacuator.
Figure 10:
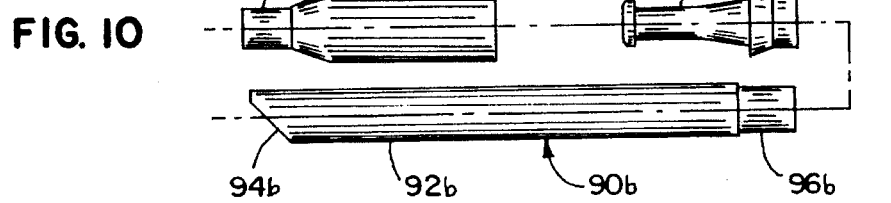
FIG. 10 is an exploded view of the assembly shown in FIG. 9.

In FIGS. 9 and 10, a valve 30b is shown attached to an evacuator 90b. Evacuators 90b are commonly used in dentistry practice by dental technicians to selectively remove saliva from a patient's mouth. Evacuator 90 has a larger diameter than an ejector such as ejector 76a to facilitate grasping of the evacuator 90b. Evacuator 90b includes a tubular straw 92b including an angled suction end 94b. Straw 92b includes a second end 96b configured to telescopingly press-fittingly engage the inside of inlet 38b. Alternatively, it is contemplated that evacuator end 96b could engage an outside of inlet 38b. Notably, valve 30b includes members 50b and 52b that are comparable to members 50 and 52 of valve 30, although members 50b and 52b have different proportions as needed for optimal flow-through characteristics when connected to evacuator end 96b.

Figure 11:
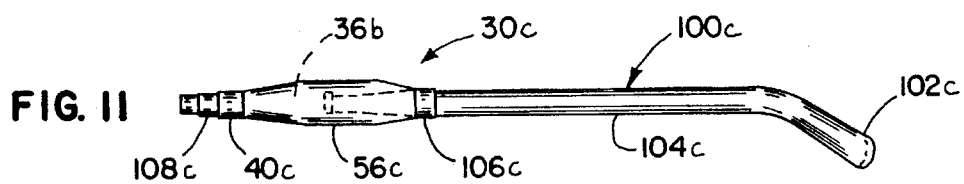
FIG. 11 is a side view of another assembly embodying the present invention including a modified fourth valve releasably connected to a disposable medical suction yankauer.
Figure 12:
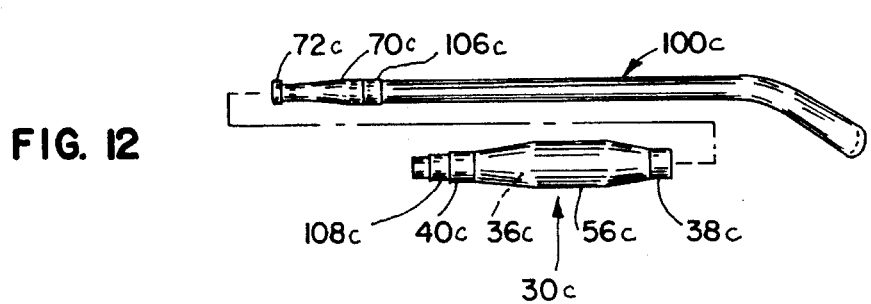
FIG. 12 is an exploded side view of the assembly shown in FIG. 11.

FIGS. 11 and 12 shows a valve 30c attached to a yankauer 100c. Yankauer 100c includes a first end 102c configured for suctioning blood or related matter, a tubular straw 104c extending from end 102c, and a second end 106c on straw 104c configured to telescopingly frictionally press-fit onto inlet 38c of valve 30c. Valve outlet 40c includes a stepped outer surface 108c such as for connecting to suction lines having different diameters. It is noted that casing 36c is shown as being one piece. However, it is contemplated that casing 36c could also be a multi-piece assembly such as is noted above in regard to valve 30a or as is noted below in regard to valve 30h.

Another valve 30d (FIGS. 13–15) includes first and second members 50d and 52d, respectively, that can be mateably engaged to form a chamber 36d and a tortuouspath-forming member 34d. An adaptor 114d is configured to mateably engage the inlet 38d. Specifically, adaptor 114d includes a ring 116d having a diameter chosen so that it frictionally sealingly engages inlet 38d, and an abutting lip 118d for engaging the end of inlet 38d to prevent overtravel of adaptor 114d into inlet 38d. Adaptor 114d further defines a second inlet 38d' having a reduced size compared to inlet 38d so that, for example, an ejector 76d can be attached to second inlet 38d'. A frustoconically-shaped wall 120d interconnects ring 116d and second inlet 38d'. FIG. 16 illustrates use of valve 30d without adaptor 114d, valve 30d being connected to an evacuator 90d.

It is contemplated that some applications may require an even more tortuous path than tortuous paths 42 of valve 30 shown in FIG. 5 and valves 30a through 30d shown in FIGS. 6–16. For this purpose, a valve 30e including a separate insert 124e (FIG. 17) is provided. Insert 124e is shaped generally similar to second member 52, but insert 124e does not include a frustoconically shaped section 62. Rather, second insert 124e is configured to fit within and frictionally engage the inside surfaces of casing 32e. More specifically, insert 124e includes tubular protruding section 68e and ring-shaped fin 72e. A circumferential rib 125e on tubular protruding section 68e extends outwardly and is configured to engage a depression 126e in cylindrically shaped wall 56e of casing 32e. It is noted that depression 126e can be located anywhere in casing 32e, and that multiple depressions 126e can be used to located multiple inserts 124e in casing 32e. Tubular protruding section 68e further includes an end 127e configured to engage the inside surface on the end of frustoconically shaped section 62e. Casing 32e is constructed of opposing members such as members 50e and 52e due to the large diameter of ring-shaped fin 72e. Notably, more than one insert 124e can be positioned in casing 32e at a time, thus greatly increasing the effective length of the tortuous path.

Another insert 129f (FIG. 18) is identical to insert 124e except that insert 129f includes a second ring-shaped fin 72f spaced longitudinally apart from first ring-shaped fin 72f on tubular protruding section 68f. Also, end 127f is formed with orthogonal surfaces. It is contemplated that even more than two fins 72f could be located on insert 129f, or that multiple inserts 124e and/or 129f could be positioned inside of casing (32e).

FIGS. 19 and 20 show a valve 30g including members 50g and 52g, and an insert 124g in combination with an evacuator 90g. Valve 30g includes a pair of reversely lipped ring-shaped fins 72g and 72g', fin 72g being on member 52g and fin 72g' being on insert 124g. Insert 124g further includes cylindrically shaped end 127g configured to securely frictionally engage the inside of casing 32g. Notably, an double finned insert as illustrated by insert 129f can be substituted for insert 124g, in which case the valve 30g would define three ring-shaped fins.

Figure 21:
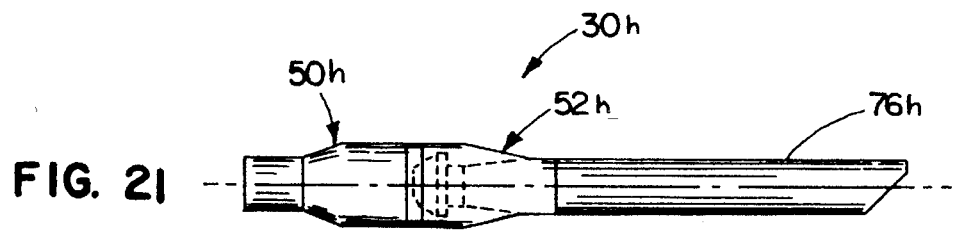
FIG. 21 is a side view of a four piece assembly embodying the present invention, the assembly including a ninth valve connected to a disposal oral evacuator.
Figure 22:
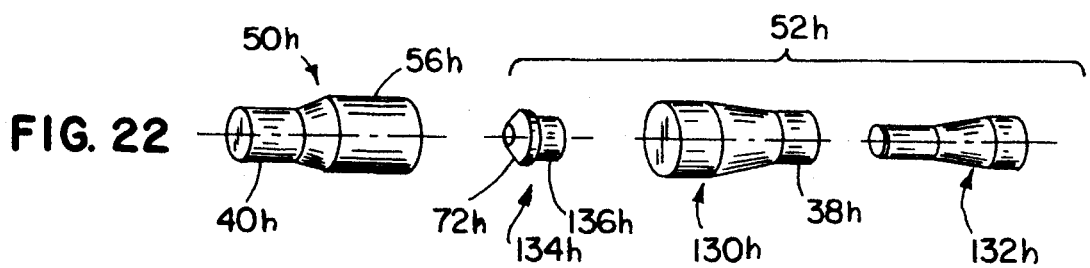
FIG. 22 is an exploded perspective view of the assembly shown in FIG. 21.
Figure 23:
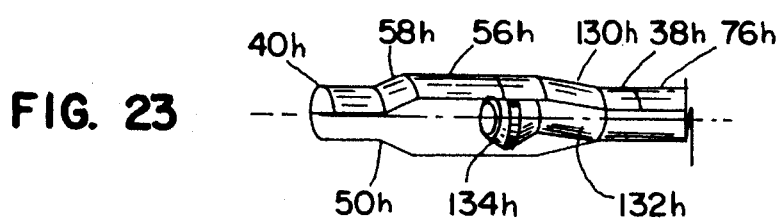
FIG. 23 is a partially broken-away perspective view of the valve shown in FIG. 21.

In FIGS. 21–23, a valve 30h is illustrated that includes members 50h and 52h. Member 52h is three piece and includes a chamber-forming shell 130h, a tubular protruding section 132h and a ring-shaped member 134h configured to mateably engage tubular protruding section 132h. Ring-shaped member 134h includes a ring-shaped fin 72h and a tubular end or stub 136h configured to frictionally engage the end of tubular protruding section 132h. Notably, it is contemplated that tubular protruding section 132h can be an integral part of another member such as an ejector 76h. To assemble member 52h, the tubular protruding section 132h is press-fittingly sealingly extended through inlet 38h of casing 32h, and tubular stub 136h on ring-shaped member 134h is frictionally engaged onto tubular protruding section 132h. Valve 30h is then assembled by press-fittingly or otherwise assembling members 50h and 52h together.

Figure 24:
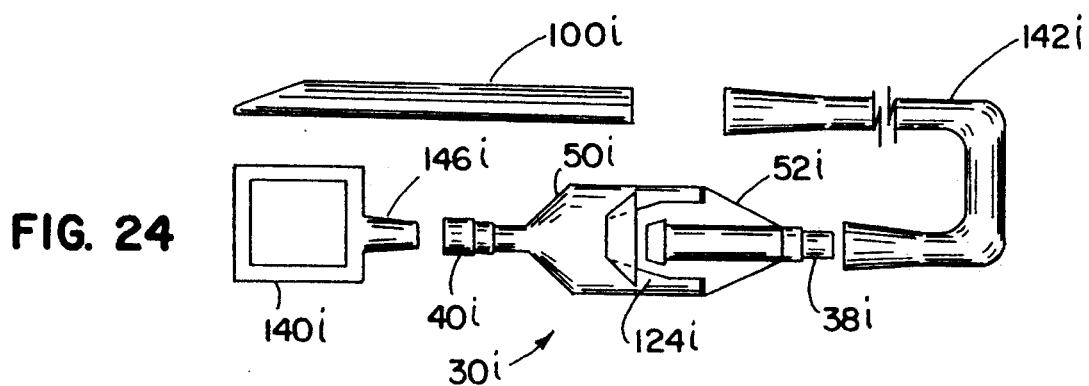
FIG. 24 is a side view of a tenth valve embodying the present invention, the valve including a pair of ring-shaped fins, the valve being connected at one end to a disposal connecting tube and a yankauer and being connected at the other end to a medical suctioning unit.
Figure 25:
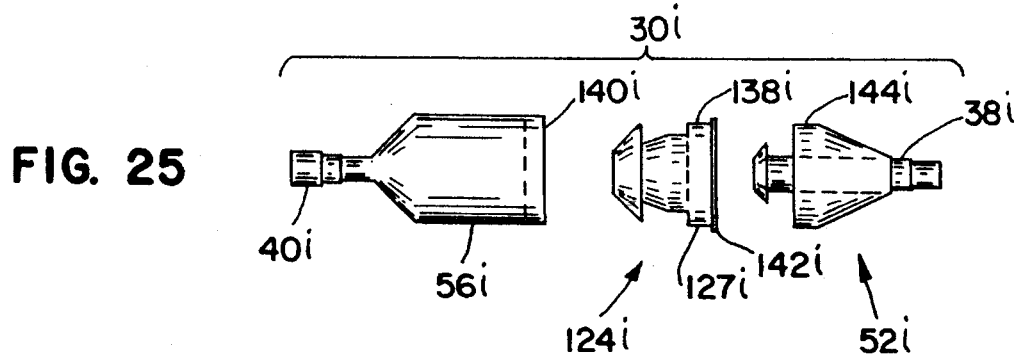
FIG. 25 is an exploded side view of the valve shown in FIG. 24.

In FIGS. 24–25, a valve 30i generally comparable to valve 30g is attached to medical suction unit 140i at outlet 40i and to a yankauer 100i by a disposable flexible tube or hose 141i. Valve 30i includes an insert 124i having an end 127i with a cylindrically shaped outer surface 138i for engaging a recess 140i in cylindrically shaped wall 56i. A radially extending surface 142i limits insertion of insert 124i into cylindrically shaped wall 56i. Member 52i includes a cylindrically shaped wall 144i sized to telescopingly slide over insert surface 142i and frictionally securely engage the outer surface of cylindrically shaped wall 56i. Valve member 52i includes an inlet 38i configured to receive flexible tube 141i, and valve member 50i includes a stepped outlet 40i configured to receive a connector 146i on medical suction unit 140i.

Thus, several valves are provided for preventing backflow of bacteria and other unhealthy substances. The valves include a casing defining a chamber and a tortuous path defining member including at least one ring-shaped fin which combine to form a tortuous path which is difficult for bacteria to traverse. The valve includes an unobstructed path for materials to be suctioned from an inlet to an outlet, but provides the tortuous path in the backflow direction from the outlet to the inlet.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The embodiments of the invention in which an exclusive property or privilege is claimed are defined as follows:

1. An antibacteria valve for use with a suction source in a medical apparatus for preventing undesired backflow of body fluid and undesired movement of bacteria, comprising:

an elongated casing defining a longitudinal direction and a chamber, said casing including an inlet and an outlet to said chamber; and a tubular member protruding from one of said inlet and said outlet including an end section protruding into said chamber, said end section having a ring-shaped fin thereon with a first portion that protrudes radially into said chamber from said end section and a second portion that extends circumferentially around said end section but that is radially spaced therefrom, said elongated casing and said tubular member including surfaces defining an unobstructed path for body fluids to flow from said inlet to said outlet, but said surfaces defining an arduous path for bacteria moving from said outlet to said inlet, whereby body fluid can be readily suctioned through said valve from said inlet to said outlet, but whereby the undesired backflow and undesired movement of bacteria through said valve is substantially prevented due to a tortuous path defined by said casing and said tubular member.

2. An antibacteria valve as defined in claim 1 wherein said chamber includes a first surface and said ring-shaped fin includes a second surface, said first and second surfaces defining the tortuous path from said outlet to said inlet.

3. An antibacteria valve as defined in claim 2 wherein said tubular member protrudes from said inlet and includes said ring-shaped fin.

4. An antibacteria valve as defined in claim 3 wherein said inlet defines a first diameter, said outlet defines a second diameter, and said ring-shaped fin defines a third diameter, said third diameter being larger than said first and second diameters.

5. An antibacteria valve as defined in claim 2 wherein said second portion of said ring-shaped fin comprises a curvilinear shape.

6. An antibacteria valve as defined in claim 2 including a pair of said ring-shaped fins.

7. An antibacteria valve as defined in claim 6 wherein said tubular member includes said pair of ring-shaped fins.

8. An antibacteria valve as defined in claim 2 wherein said casing includes a first tubular section and a second tubular section, said first and second tubular sections being configured to mateably sealingly engage to enclose and support said ring-shaped fin.

9. An antibacteria valve as defined in claim 8 wherein said tubular member includes an end configured to engage and support said ring-shaped fin.

10. An antibacteria valve as defined in claim 2 wherein said casing and said tubular member are configured to be friction-fit together to form a leak free joint.

11. An antibacteria valve as defined in claim 2 wherein said elongated casing and said tubular member are made of plastic.

12. An antibacteria valve as defined in claim 2 wherein said ring-shaped fin is oriented at an angle to said longitudinal direction and extends partially in a longitudinal direction from said outlet toward said inlet.

13. An antibacteria valve as defined in claim 1 wherein said casing includes a first part defining said inlet and a second part defining said outlet, said first and second part being mateably sealingly engaged to form said chamber.

14. An antibacteria valve as defined in claim 13 wherein said first part includes said tubular member.

15. An antibacteria valve as defined in claim 13 including a third part defining said ring-shaped fin and a portion of said tubular member, and further including a tubular fourth part extending through and engaging one of said inlet and said outlet to support said third part.

16. An antibacteria valve as defined in claim 1 wherein said tubular member includes a tubular section configured to receive an evacuator.

17. An antibacteria valve as defined in claim 1 wherein one of said tubular member and said inlet are configured to receive an evacuator, and including an adapter engaged with said one tubular member and inlet, said adapter including a second inlet configured to connect to an ejector.

18. A medical suctioning apparatus including a medical suction unit and a Yankauer structure and further including an anti-bacteria valve as defined in claim 1, said anti-bacteria valve interconnecting said medical suction unit to said Yankauer structure.

19. A valve for use with a suctioning device in a medical apparatus for preventing undesired movement of bacteria between first and second tubular members, comprising:

a casing including an annular elongated wall defining a longitudinal direction and a centerline, said casing including an inner surface which defines a chamber, said wall further defining an inlet connected to said first tubular member and an outlet connected to said second tubular member; and an annular tubular member positioned in said chamber, said annular tubular member including a tubular section and a fin having ring-shaped surfaces that extend in a radial direction away from said centerline in said chamber and further that extend in said longitudinal direction, said ring-shaped surfaces including a portion that extends circumferentially around and is spaced from said tubular section, said chamber inner surface and said ring-shaped surfaces defining a tortuous path having a length significantly longer than a linear distance from said inlet to said outlet, whereby body fluids can be readily suctioned through said valve from said inlet to said outlet, but whereby undesired backflow of body fluid and undesired movement of bacteria through said valve along said inner surface and said ring-shaped surfaces is substantially prevented due to the tortuous path defined by said inner surfaces and said ring-shaped surfaces.

20. A valve as defined in claim 19 wherein said ring-shaped surfaces are curvilinear.

21. A valve as defined in claim 20 including a pair of said ring-shaped surfaces.

22. An antibacteria valve comprising:

a casing defining a chamber, an inlet and an outlet; and a tortuous-path-forming member positioned in said chamber including a section with surfaces defining a tortuous path, said tortuous-path-forming member including at least one insert and with a tubular section a ring-shaped fin that extends circumferentially around said tubular section and that is spaced radially therefrom, whereby undesired movement of bacteria through said valve is substantially prevented due to the tortuous path defined by said surfaces.

23. An antibacteria valve as defined in claim 22 wherein said inlet includes a diameter, and said section has a diameter smaller than the diameter of said inlet.

24. An antibacteria valve as defined in claim 22 wherein said inlet and said outlet define a longitudinal direction, and said tortuous-path-forming surfaces include angled surfaces oriented at an angle to said longitudinal direction.

25. An antibacteria valve as defined in claim 22 wherein said insert frictionally and sealingly engages said inlet.

26. An antibacteria valve comprising:

a first casing section defining an inlet;

a second casing section defining an outlet, said first and second casing sections being being mateably sealingly engaged to define a chamber; and a tortuous-path-forming member located in said chamber between said first and second casing sections, said tortuous-path-forming member including at least one tubular insert and a ring-shaped fin having a portion that extends circumferentially around said tubular insert and that is spaced radially therefrom, said tortuous path defining a length that is longer than a distance from said inlet to said outlet plus a length of said tubular insert in said chamber.

27. An antibacteria valve as defined in claim 26 wherein said inlet defines a first diameter, said outlet defines a second diameter and said ring-shaped fin defines a third diameter, said third diameter being larger than said first and second diameters.

28. An antibacteria valve as defined in claim 27 wherein said tortuous-path-forming member includes surfaces oriented at an angle to said longitudinal direction.

29. An antibacteria valve as defined in claim 26 wherein said tortuous-path-forming member is an integral part of said first casing section.

30. An antibacteria valve as defined in claim 26 including a second tortuous-path-forming member located in said chamber between said first and second casing sections.

* * * * *